US011648071B2

(12) United States Patent
Thienphrapa et al.

(10) Patent No.: US 11,648,071 B2
(45) Date of Patent: May 16, 2023

(54) AUTONOMOUS X-RAY CONTROL FOR ROBOTIC NAVIGATION

(71) Applicant: KONINKLIJKE PHILIPS N.V., Eindhoven (NL)

(72) Inventors: Paul Thienphrapa, Cambridge, MA (US); Molly Lara Flexman, Melrose, MA (US); Torre Michelle Bydlon, Melrose, MA (US); Aleksandra Popovic, Boston, MA (US); Marcin Arkadiusz Balicki, Cambridge, MA (US); Grzegorz Andrzej Toporek, Boston, MA (US); Alexandru Patriciu, Belmont, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 242 days.

(21) Appl. No.: 16/762,630

(22) PCT Filed: Nov. 12, 2018

(86) PCT No.: PCT/EP2018/080852
§ 371 (c)(1),
(2) Date: May 8, 2020

(87) PCT Pub. No.: WO2019/092225
PCT Pub. Date: May 16, 2019

(65) Prior Publication Data
US 2020/0275982 A1 Sep. 3, 2020

Related U.S. Application Data

(60) Provisional application No. 62/585,193, filed on Nov. 13, 2017.

(51) Int. Cl.
*A61B 34/32* (2016.01)
*B25J 9/16* (2006.01)
(Continued)

(52) U.S. Cl.
CPC ............. *A61B 34/32* (2016.02); *B25J 9/1664* (2013.01); *B25J 9/1694* (2013.01); *A61B 6/481* (2013.01);
(Continued)

(58) Field of Classification Search
CPC .................. A61B 34/32; A61B 6/481; A61B 2034/107; A61B 2034/2065; A61B 2090/376;
(Continued)

(56) References Cited

U.S. PATENT DOCUMENTS

| 8,971,490 B2 | 3/2015 | Maurer |
| 2003/0073901 A1 | 4/2003 | Simon |

(Continued)

FOREIGN PATENT DOCUMENTS

| WO | 2012011035 | 1/2012 |
| WO | 2012/077011 | 6/2012 |

OTHER PUBLICATIONS

International Search Report and Written Opinion dated Feb. 2, 2019 for International Application No. PCT/EP2018/080852 Filed Nov. 12, 2018.

(Continued)

*Primary Examiner* — Joel Lamprecht (57) ABSTRACT

An intervention system employing an interventional robot (30), an interventional imaging modality (10) and an interventional controller (70). In 5 operation, the interventional controller (70) navigates an anatomical roadmap (82) of an anatomical region of a patient in accordance with an interventional plan to thereby control a navigation of the interventional robot (30) within the anatomical region in accordance with the anatomical roadmap (82). Upon a detection by the interventional controller (70) of an occurrence of the interventional controller (70) navigating 10 proximately to a critical anatomical location within the anatomical roadmap (Continued)

(82), the interventional controller (70) pauses the navigation of the interventional robot (30) within anatomical region and autonomously controls an operation of the interventional imaging modality (10) for generating an updated anatomical roadmap (82) of the anatomical region whereby the interventional controller (70) navigates the updated 15 anatomical roadmap (82) of the anatomical region in accordance with the interventional plan to thereby control a resumed navigation of the interventional robot (30) within the anatomical region.

20 Claims, 3 Drawing Sheets (51) Int. Cl.
*A61B 34/10* (2016.01)
*A61B 34/20* (2016.01)
*A61B 90/00* (2016.01)
*A61B 6/00* (2006.01)

(52) U.S. Cl.
CPC .............. *A61B 2034/107* (2016.02); *A61B 2034/2065* (2016.02); *A61B 2090/376* (2016.02); *A61B 2090/3764* (2016.02)

(58) Field of Classification Search
CPC .......... A61B 2090/3764; A61B 5/0205; A61B 5/021; A61B 5/024; A61B 5/055; A61B 5/0816; A61B 5/14551; A61B 5/318; A61B 8/0841; A61B 2034/2046; A61B 2090/3612; A61B 2090/374; A61B 2090/3762; A61B 2090/378; A61B 2505/05; A61B 34/10; A61B 34/20; A61B 34/37; A61B 90/37; A61B 6/12; A61B 6/4441; A61B 2034/301; A61B 2560/029; B25J 9/1664; B25J 9/1694; A61F 2/2427
See application file for complete search history.

(56) References Cited

U.S. PATENT DOCUMENTS

| | | | |
|---|---|---|---|
| 2007/0167700 A1 | 7/2007 | Rahn | |
| 2009/0234444 A1 | 9/2009 | Maschke | |
| 2011/0038518 A1 | 2/2011 | Spahn | |
| 2013/0261439 A1* | 10/2013 | Schmitt | ................. A61B 5/055 600/424 |
| 2015/0164605 A1 | 6/2015 | Patwardhan | |

OTHER PUBLICATIONS

Gorges, et al: "3D Augmented Fluoroscopy in Interventional Neuroradiology: Precision Assessment and First Evaluation on Clinical Cases", Aug. 2009.

Atasoy, et al: "Real-Time Respiratory Motion Tracking: Roadmap Correction for Hepatic Artery Catheterizations". Proc. of SPIE vol. 6918, 691815, (2008).

* cited by examiner

AUTONOMOUS X-RAY CONTROL FOR ROBOTIC NAVIGATION

CROSS REFERENCE TO RELATED APPLICATIONS

This application is the U.S. National Phase application under 35 U.S.C. § 371 of International Application No. PCT/EP2018/080852 filed Nov. 12, 2018, published as WO 2019/092225 on May 16, 2019, U.S. Provisional Patent Application No. 62/585,193 filed Nov. 13, 2017. These applications are hereby incorporated by reference herein.

FIELD OF THE INVENTION

The present disclosure generally relates to an X-ray image based navigation of a robot within an anatomical region. The present disclosure specifically relates to novel and inventive autonomous X-ray control for navigation of the robot within the anatomical region.

BACKGROUND OF THE INVENTION

Many intervention systems as known in the art of the present disclosure utilized live X-ray for assistance in a navigation by a clinician of a intervention instrument within a patient during an interventional procedure. This may lead to radiation exposure to not only the patient, but to the clinician and associated staff as well. This potential problem is made evident by radiation shielding in an attempt to impede the radiation exposure. However, radiation shielding at times has proven to force awkward positioning of the patient and/or the clinician and further force the clinician to wear a lead apron. This may result in chronic orthopedic ailments for the clinician, and a development of tumors around the arms, head, neck, and other unshielded parts of the clinician's body.

In the common practice of such X-ray image based navigation of a surgical instrument, the clinician activates live X-ray imaging using a foot pedal in order to see the interventional instrument as the clinician navigates the interventional instrument within the patient's body. Under this practice, the clinician will tend to run the live X-ray continuously, which compounds the aforementioned problems associated with potential radiation exposure to the clinician.

SUMMARY OF THE INVENTION

The inventions of the present disclosure facilitate a reduction in radiation exposure in an interventional setting by providing an interventional controller for a robotic navigation of an interventional instrument based on a single static anatomical roadmap that is automatically updated by the interventional controller when the robot reaches a critical navigation position within the anatomical roadmap and/or when a physiological status of the patient is critical.

One embodiment of the inventions of the present disclosure is an intervention system employing an interventional robot, an interventional imaging modality and an interventional controller. The interventional robot is operable to be navigated within an anatomical region of a patient, and the interventional imaging modality is operable for imaging the anatomical region of the patient.

To control an execution of an interventional procedure by the interventional robot and the interventional imaging modality, the interventional controller is configured to (1) navigate an anatomical roadmap of the anatomical region of the patient in accordance with an interventional plan, (2) autonomously control a navigation of the interventional robot within the anatomical region of the patient in accordance with the navigation by the interventional controller of the anatomical roadmap of the anatomical region, and (3) detect any occurrence of the interventional controller reaching a critical anatomical location within the anatomical roadmap.

Upon a detection by the interventional controller navigating proximately to the critical anatomical location within the anatomical roadmap, the interventional controller is further configured to (4) pause the navigation of the interventional robot within anatomical region of the patient, (5) autonomously control an interventional imaging of the anatomical region of the patient by the interventional imaging modality, (6) generate an updated anatomical roadmap of the anatomical region from the interventional imaging of the anatomical region of the patient, (7) navigate the updated anatomical roadmap of the anatomical region of the patient in accordance with the interventional plan, and (8) autonomously control a resumed navigation of the interventional robot within the anatomical region of the patient in accordance with the navigation by the interventional controller of the updated anatomical roadmap of the anatomical region.

A second embodiment of the inventions of the present disclosure is the interventional controller employing a modality control module and a robot control module interactive to control the execution of the interventional procedure by the interventional robot and the interventional imaging modality.

The robot control module is configured to (1) navigate an anatomical roadmap of the anatomical region of the patient in accordance with an interventional plan, (2) autonomously control a navigation of the interventional robot within the anatomical region of the patient in accordance with the navigation by the interventional controller of the anatomical roadmap of the anatomical region, and (3) detect any occurrence of the interventional controller reaching a critical anatomical location within the anatomical roadmap.

Upon a detection by the robot control module of an occurrence of the interventional controller navigating proximately to a critical anatomical location within the anatomical roadmap, the robot control module is further configured to (4) pause the navigation of the interventional robot within anatomical region of the patient and the modality control module is configured to (5) autonomously control an interventional imaging of the anatomical region of the patient by the interventional imaging modality and (6) generate an updated anatomical roadmap of the anatomical region from the interventional imaging of the anatomical region of the patient, whereby the robot control module is further configured to (7) navigate the updated anatomical roadmap of the anatomical region of the patient in accordance with the interventional plan, and (8) autonomously control a resumed navigation of the interventional robot within the anatomical region of the patient in accordance with the navigation by the interventional controller of the updated anatomical roadmap of the anatomical region.

A third embodiment of the inventions of the present disclosure is an intervention method for an intervention system including an interventional robot operable to be navigated within an anatomical region of a patient, an interventional imaging modality operable for an interventional imaging of the anatomical region of the patient, and an interventional controller operable for controlling an execution of an interventional procedure by the interventional robot and the interventional imaging modality.

The intervention method comprises the interventional controller (1) navigating an anatomical roadmap of the anatomical region of the patient in accordance with an interventional plan, (2) controlling a navigation of the interventional robot within the anatomical region of the patient in accordance with the navigation by the interventional controller of the anatomical roadmap of the anatomical region, and (3) detecting any occurrence of the interventional controller reaching a critical anatomical location within the anatomical roadmap.

Upon a detection by the interventional controller navigating proximately to the critical anatomical location within the anatomical roadmap, the intervention method further comprises the interventional controller (4) pausing the navigation of the interventional robot within anatomical region of the patient, (5) autonomously controlling an interventional imaging of the anatomical region of the patient by the interventional imaging modality, (6) generating an updated anatomical roadmap of the anatomical region from the interventional imaging of the anatomical region of the patient, (7) navigating the updated anatomical roadmap of the anatomical region of the patient in accordance with the interventional plan, and (8) controlling a resumed navigation of the interventional robot within the anatomical region of the patient in accordance with the navigation by the interventional controller of the updated anatomical roadmap of the anatomical region.

For purposes of describing and claiming the inventions of the present disclosure:

(1) terms of the art of the present disclosure including, but not limited to, "interventional procedure", "interventional robot", "interventional imaging modality" and "anatomical roadmap" are to be broadly interpreted as known in the art of the present disclosure and exemplary described in the present disclosure;

(2) more particularly, the term "interventional procedure" broadly encompasses all interventional procedures, as known in the art of the present disclosure or hereinafter conceived, for an imaging, a diagnosis and/or a treatment of a patient anatomy;

(3) more particularly, the term "interventional robot" broadly encompasses all robotic systems, as known in the art of the present disclosure and hereinafter conceived, utilized during an interventional procedure. Examples of an interventional robot include, but is not limited to, serial articulated robot arms employed by the da Vinci® Robotic System, the Medrobotics Flex® Robotic System, the Magellan™ Robotic System, and the CorePath® Robotic System;

(4) more particularly, the term "interventional imaging modality" broadly encompasses all interventional imaging modality, as known in the art of the present disclosure and hereinafter conceived, utilized during an interventional procedure. Examples of an interventional imaging modality include, but is not limited to, an X-ray interventional imaging modality, an ultrasound interventional imaging modality, a computed tomography interventional imaging modality and a magnetic resonance interventional imaging modality;

(5) more particularly, the term "anatomical roadmap" broadly encompasses all anatomical roadmap formats, as known in the art of the present disclosure and hereinafter conceived, illustrating any and all natural pathways through a patient anatomy that are navigational by an interventional robot. Examples of an anatomical roadmap include, but are not limited to, a preoperative or an intraoperative segmented image of an entirety or a partial illustration of blood vessel(s) or bronchial tube(s);

(6) the term "critical anatomical location" encompasses a location within an anatomical roadmap defined by an intervention system of the present disclosure as a location within an anatomical roadmap that necessitates a generation of an updated anatomical roadmap for purposes of facilitating a navigation of an interventional robot within the patient anatomy. Examples of a critical anatomical location include, but are not limited to, a location within an anatomical roadmap corresponding to an anatomical branch (e.g., a branch in a respiratory system of a patient), corresponding to an exit point of the anatomical roadmap, corresponding to a surface of an anatomical structure, corresponding to a range of motion of the anatomical structure, corresponding to an interventional task in accordance with the intervention plan, or corresponding to an application of force by the interventional robot upon an anatomical structure within the anatomical region;

(7) the term "critical physiological status" of a patient encompasses a physiological status of patient during an interventional procedure that is defined by an intervention system of the present disclosure as a physiological status of the patient that necessitates a generation of an updated anatomical roadmap for purposes of facilitating a navigation of an interventional robot within the patient anatomy. An example of a critical physiological status of a patient includes, but is not limited to, basic physiological parameters (e.g., respiration, heart rate, etc.) of the patient indicating an unacceptable risk of anxiety, panic, claustrophobic episodes, etc. in a patient during an interventional procedure;

(8) the term "controller" broadly encompasses all structural configurations, as understood in the art of the present disclosure and as exemplary described in the present disclosure, of an application specific main board or an application specific integrated circuit for controlling an application of various inventive principles of the present disclosure as subsequently described in the present disclosure. The structural configuration of the controller may include, but is not limited to, processor(s), computer-usable/computer readable storage medium(s), an operating system, application module(s), peripheral device controller(s), slot(s) and port(s). A controller may be housed within or linked to a workstation. Examples of a "workstation" include, but are not limited to, an assembly of one or more computing devices, a display/monitor, and one or more input devices (e.g., a keyboard, joysticks and mouse) in the form of a standalone computing system, a client computer of a server system, a desktop, a laptop or a tablet;

(9) the descriptive labels for controllers described and claimed herein facilitate a distinction between controllers as described and claimed herein without specifying or implying any additional limitation to the term "controller";

(10) the term "application module" broadly encompasses an application incorporated within or accessible by a controller consisting of an electronic circuit (e.g., electronic components and/or hardware) and/or an executable program (e.g., executable software stored on non-transitory computer readable medium(s) and/or firmware) for executing a specific application;

(11) the descriptive labels for application modules described and claimed herein facilitate a distinction between application modules as described and claimed herein without specifying or implying any additional limitation to the term "controller";

(12) the terms "signal", "data" and "command" broadly encompasses all forms of a detectable physical quantity or impulse (e.g., voltage, current, or magnetic field strength) as understood in the art of the present disclosure and as exemplary described in the present disclosure for transmitting information and/or instructions in support of applying various inventive principles of the present disclosure as subsequently described in the present disclosure. Signal/data/command communication various components of the present disclosure may involve any communication method as known in the art of the present disclosure including, but not limited to, signal/data/command transmission/reception over any type of wired or wireless datalink and a reading of signal/data/commands uploaded to a computer-usable/computer readable storage medium; and (13) the descriptive labels for signals/data/commands as described and claimed herein facilitate a distinction between signals/data/commands as described and claimed herein without specifying or implying any additional limitation to the terms "signal", "data" and "command".

The foregoing embodiments and other embodiments of the inventions of the present disclosure as well as various structures and advantages of the inventions of the present disclosure will become further apparent from the following detailed description of various embodiments of the inventions of the present disclosure read in conjunction with the accompanying drawings. The detailed description and drawings are merely illustrative of the inventions of the present disclosure rather than limiting, the scope of the inventions of the present disclosure being defined by the appended claims and equivalents thereof.

DETAILED DESCRIPTION OF THE PREFERRED EMBODIMENTS

Figure 1:
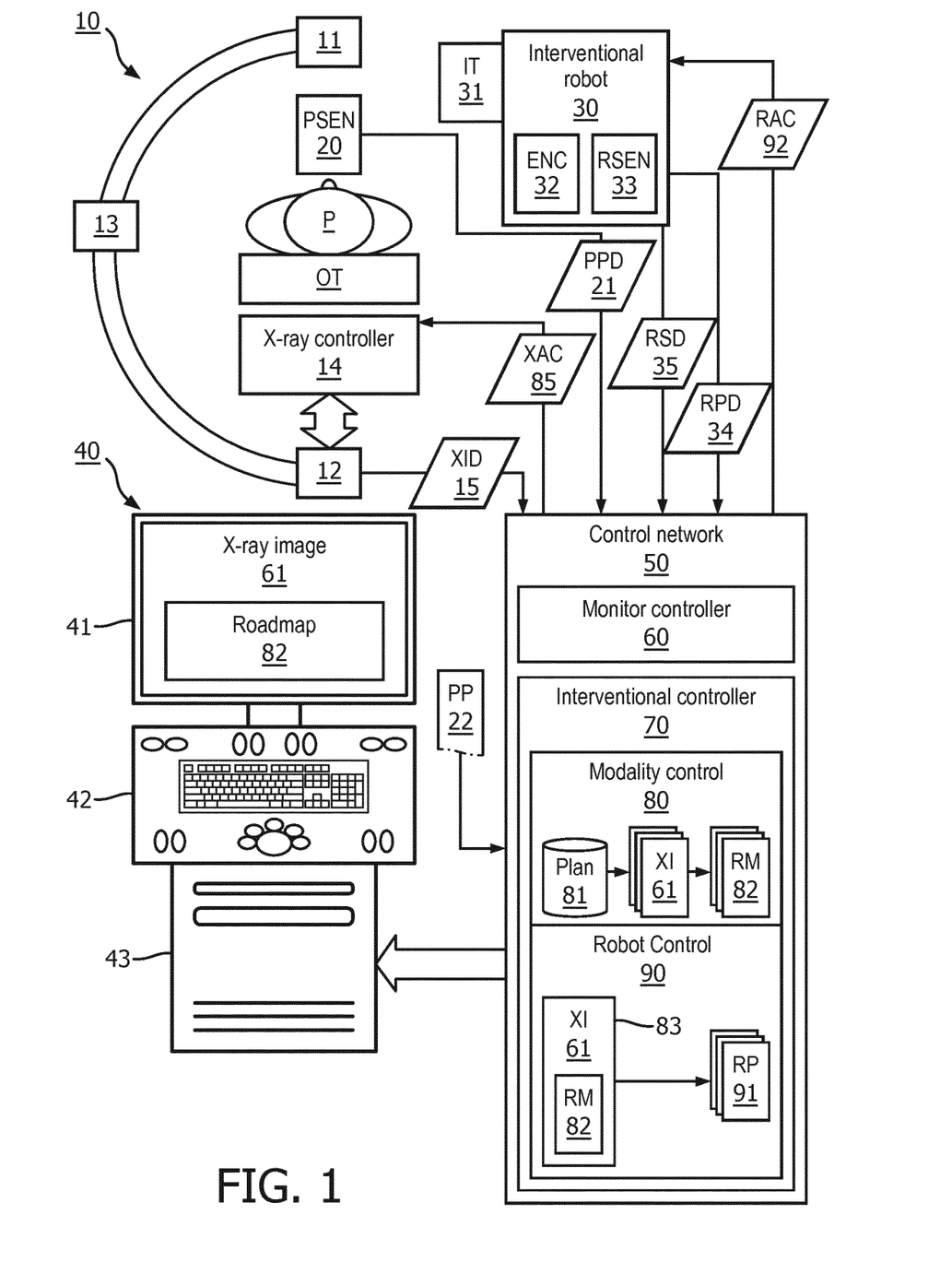
FIG. 1 illustrates a first exemplary embodiment of an intervention system in accordance with the inventive principles of the present disclosure.

To facilitate an understanding of the various inventions of the present disclosure, the following description of FIG. 1 teaches basic inventive principles associated with intervention systems of the present disclosure incorporating an X-ray interventional imaging modality. From this description, those having ordinary skill in the art will appreciate how to apply the inventive principles of the present disclosure for making and using additional embodiments of intervention systems of the present disclosure incorporating any type of interventional imaging modality.

Referring to FIG. 1, an intervention system of the present disclosure employs a X-ray modality 10 (e.g., a mobile c-arm as shown), patient sensors 20, an interventional robot 30, an intervention workstation 40 and a control network 50 for deploying an interventional tool 31 held by interventional robot 30 within an anatomical region of a patient P lying prone on an operating table OT during an interventional procedure of any type.

As known in the art of the present disclosure, X-ray modality 10 generally includes an X-ray generator 11, an image intensifier 12 and a collar 13 for rotating X-ray modality 10. In operation as known in the art, an X-ray controller 14 controls a generation by X-ray modality 10 of X-ray imaging data 15 informative of a X-ray imaging of the anatomical region of patient P (e.g., a heart of patient P during a minimally invasive aortic valve replacement).

In practice, X-ray controller 14 may be installed within an X-ray imaging workstation (not shown), or alternatively installed within intervention workstation 40.

Still referring to FIG. 1, interventional robot 30 is any type of robot utilized for interventional procedures as known in the art in the art of the present disclosure, such as, for example, the da Vinci® Robotic System, the Medrobotics Flex® Robotic System, the MagellanTM Robotic System, and the CorePath® Robotic System.

Patient sensors 20 are any type of sensor utilized for generating patient physiological data 21 informative of one or more physiological parameters of patient P during an interventional procedure. Examples of a physiological parameter include, but are not limited, to a respiration rate and a heart rate of patient P.

Interventional robot 30 includes an intervention tool 31, one or more encoders 33 and one or more robot sensors 33.

Intervention tool 31 is any type of intervention tool utilized for interventional procedures. Examples of intervention tool 31 include, but are not limited to, artificial heart devices, closure devices, suction devices, punches, catheters, balloon catheters, ablation catheters, stents and grafts.

Encoder(s) 32 are any type of encoder as known in the art of the present disclosure for generating robot pose data 34 informative of a location and/or orientation of each arm/link of interventional robot 30 relative to a reference to thereby facilitate a determination by an interventional controller 70 of a pose of intervention tool 31 as held by interventional robot 30 within the anatomical region of patient P.

Robot sensor(s) 33 are any type of sensor as known in the art of the present disclosure for generating robot sensor data 35 informative of a parameter associated with interventional robot 30. An example of robot sensor(s) 33 includes, but not limited to, force sensor(s) as known in the art of the present disclosure for generating robot sensor data 35 informative of a degree of any force applied by interventional robot 30 via interventional tool 31 or robot 30 itself to tissue within the anatomical region of patient P.

Still referring to FIG. 1, intervention workstation 40 is assembled in a known arrangement of a standalone computing system employing a monitor 41, a keyboard 42 and a computer 43.

Control network 50 is installed on computer 43, and employs monitor controller 60 and interventional controller 70.

As installed on computer 43, control network 50 includes processor(s), memory, a user interface, a network interface, and a storage interconnected via one or more system buses.

Each processor may be any hardware device, as known in the art of the present disclosure or hereinafter conceived, capable of executing instructions stored in memory or storage or otherwise processing data. In a non-limiting example, the processor may include a microprocessor, field programmable gate array (FPGA), application-specific integrated circuit (ASIC), or other similar devices.

The memory may include various memories, as known in the art of the present disclosure or hereinafter conceived, including, but not limited to, L1, L2, or L3 cache or system memory. In a non-limiting example, the memory may include static random access memory (SRAM), dynamic RAM (DRAM), flash memory, read only memory (ROM), or other similar memory devices.

The user interface may include one or more devices, as known in the art of the present disclosure or hereinafter conceived, for enabling communication with a user such as an administrator. In a non-limiting example, the user interface may include a command line interface or graphical user interface that may be presented to a remote terminal via the network interface.

The network interface may include one or more devices, as known in the art of the present disclosure or hereinafter conceived, for enabling communication with other hardware devices. In an non-limiting example, the network interface may include a network interface card (NIC) configured to communicate according to the Ethernet protocol. Additionally, the network interface may implement a TCP/IP stack for communication according to the TCP/IP protocols. Various alternative or additional hardware or configurations for the network interface will be apparent\

The storage may include one or more machine-readable storage media, as known in the art of the present disclosure or hereinafter conceived, including, but not limited to, read-only memory (ROM), random-access memory (RAM), magnetic disk storage media, optical storage media, flash-memory devices, or similar storage media. In various non-limiting embodiments, the storage may store instructions for execution by the processor or data upon with the processor may operate. For example, the storage may store a base operating system for controlling various basic operations of the hardware. The storage stores one or more application modules in the form of executable software/firmware for implementing the various functions of monitor controller 60 and interventional controller 70 as further described in the present disclosure.

Monitor controller 60 and interventional controller 70 may be segregated, or partially or entirely integrated within computer 43. Alternatively, monitor controller 60 and interventional controller 70 may be distributed in any manner between two (2) workstations 40.

Still referring to FIG. 1, monitor controller 60 processes X-ray image data 15 to generate an X-ray image 61 and controls a display of X-ray image 61 on monitor 41 as known in the art of the present disclosure. Monitor controller 60 further controls a display on monitor 41 of an overlay or a fusion 86 of a roadmap 82 onto X-ray image 74.

Interventional controller 70 includes an modality control 80 and a robot control 90 as application modules for implementing a controlled navigation of interventional robot 30 within the anatomical region of patient P.

Modality control 80 is configured to generate an anatomical roadmap 82 as known in the art of the present disclosure. In one embodiment, modality control 80 accesses an intervention plan 81 stored within or accessible by intervention workstation 40 that delineates a robotic path through a segmented X-ray image of the anatomical region of patient P to implement the interventional procedure (e.g., a robotic path delineated within a X-ray image of a thoracic anatomical region of patient P during a minimally invasive aortic valve replacement). Modality control 80 further accesses an X-ray image 61 of the anatomical region of patient P (e.g., a three-dimensional (3D) X-ray image of the anatomical region of patient P or a series of spatial two-dimensional X-ray images of the anatomical region of patient P forming a 3D X-ray image) to thereby extract anatomical roadmap 82 from X-ray image 61 corresponding to the robotic path within the anatomical region of patient P delineated by the intervention plan 81.

Robot control 90 is configured to generate robot poses 91 as robot control 90 navigates through anatomical roadmap 82, which may be overlaid or fused with X-ray image 61, and to communicate robot actuation commands 92 to interventional robot 30 whereby robot actuation commands 92 instruct interventional robot 30 for actuation corresponding to robot poses 91.

In practice, modality control 80 and robot control 90 interactively execute a roadmap updating routine of the present disclosure. To facilitate a further understanding of the various inventions of the present disclosure, the following description of FIG. 2 teaches basic inventive principles associated with intervention methods of the present disclosure incorporating a roadmap updating routine in the context of a minimally invasive aortic valve replacement as implemented by the intervention system of FIG. 1. From this description, those having ordinary skill in the art will appreciate how to apply the inventive principles of the present disclosure for making and using additional embodiments of intervention methods of the present disclosure incorporating a roadmap updating routine in the context of any interventional procedure.

Figure 2:
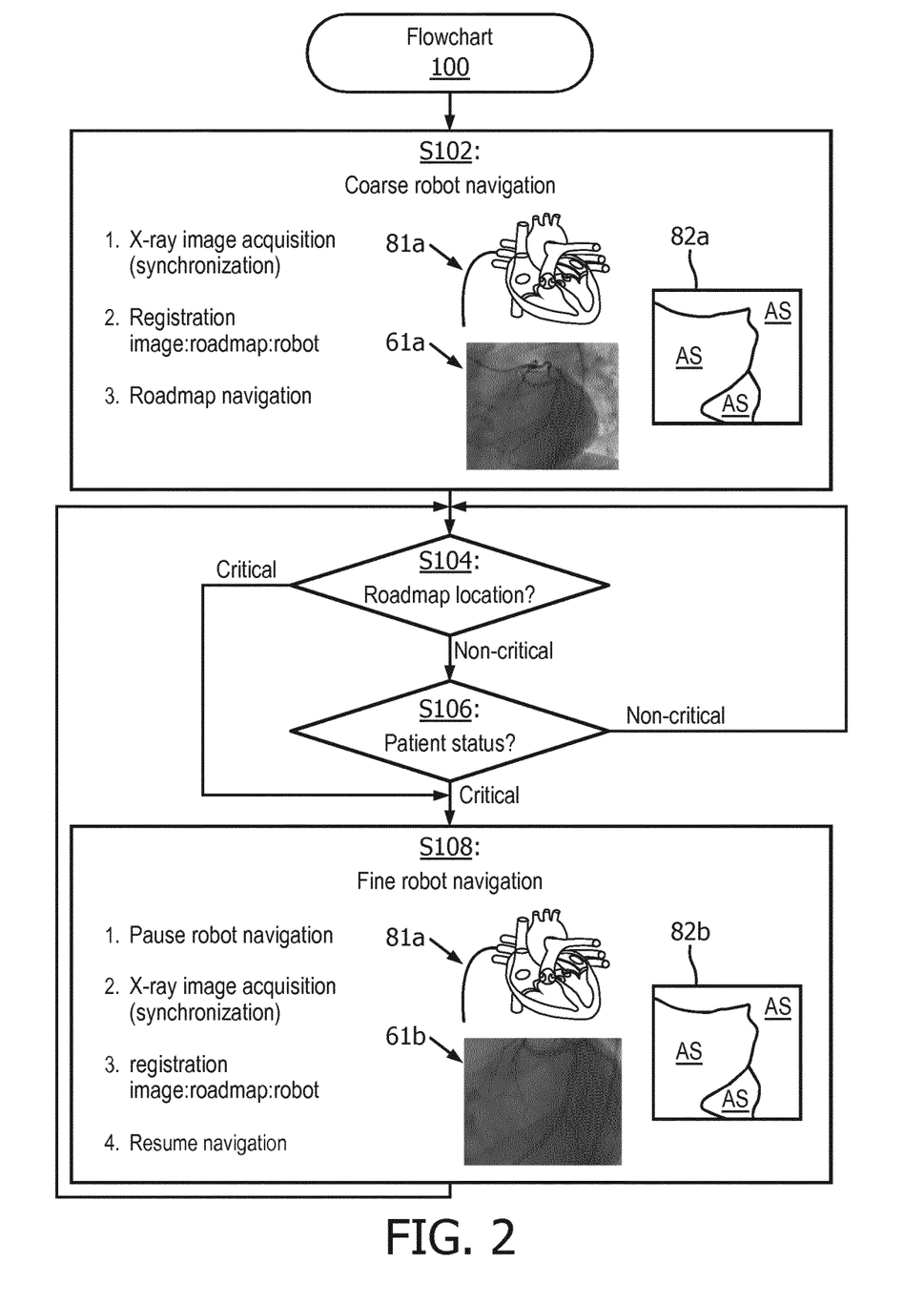
FIG. 2 illustrates a flowchart representative of an exemplary embodiment of an intervention method in accordance with the inventive principles of the present disclosure.

Referring to FIG. 2, a flowchart 100 is representative an intervention method of the present disclosure incorporating a roadmap updating routine in the context of a minimally invasive aortic valve replacement.

Referring to FIGS. 1 and 2, a stage S102 of flowchart 100 encompasses a coarse robot navigation at the beginning of the procedure that involves modality control 80 (1) controlling X-ray modality 10 for preoperatively or intraoperatively acquiring an X-ray image 61a of a heart of patient P in accordance with an intervention plan 81a to thereby generate an anatomical roadmap 82a, preferably a low resolution X-ray image 61a and (2) registering X-ray image 61a, anatomical roadmap 82a and interventional robot 30 as known in the art of the present disclosure. In one embodiment, roadmap 82a is generated from a X-ray image 61a by applying image processing techniques of known in the art of the present disclosure including an edge detection to reveal boundaries of anatomical structures, a thresholding to remove noise and minor variances in pixel values, and a segmentation and classification to identify connected anatomical structures. Once the anatomical structure is revealed, the anatomical structure may be referenced semantically to a clinical model to determine a path within X-ray image 61a for robot 30 to traverse. The path is determined in the coordinate system of the X-ray image 61a, and the image is registered to robot 30 via registration techniques as known in the art of the present disclosure, thus informing the robot's trajectory.

The coarse robot navigation further involves robot control 90 (3) navigating anatomical roadmap 82a in accordance with intervention plan 81a to thereby generate robot actuation commands 92 whereby interventional robot 30 correspondingly navigates through the anatomical region of patient P.

This navigation is considered a coarse robot navigation because the field-of-view of the anatomical roadmap 82a is intended to be of a wider area of pathways through one or more anatomical structures AS to facilitate a faster, less precise navigation of anatomical roadmap 82a.

While robot control 90 is navigating anatomical roadmap 82a, a stage S104 of flowchart 100 encompasses robot control 90 ascertaining whether or not robot control 90 is proximate to non-critical anatomical location(s) within anatomical roadmap 82a. In one embodiment, robot control 90 determines if a location of robot control 90 within anatomical roadmap 82a is at or within a defined vector from the critical anatomical location.

A critical anatomical location of anatomical roadmap 82a is a location within anatomical roadmap 82a defined by the intervention system as a location within anatomical roadmap 82a that necessitates a generation of an updated anatomical roadmap 82 for purposes of facilitating a navigation of interventional robot 30 within the anatomical region of patient P.

Examples of a critical anatomical location include, but are not limited to, a location within anatomical roadmap 82a corresponding to an anatomical branch (e.g., a branch in a respiratory system of a patient), corresponding to an exit point of the anatomical roadmap 82a, corresponding to a surface of an anatomical structure AS, corresponding to a range of motion of an anatomical structure AS, corresponding to an interventional task in accordance with the intervention plan 81a, or corresponding to an application of force by the interventional robot 30 upon an anatomical structure AS.

Any anatomical location not defined by the intervention system as a critical anatomical location is considered a non-critical anatomical location by default.

If robot control 90 ascertains robot control 90 is not proximate to a critical anatomical location within anatomical roadmap 82a, then robot control 90 proceeds to a stage S106 of flowchart 100 to ascertain whether or not a physiological status of patient P is critical. In one embodiment, robot control 90 compares patient physiological data 21 (FIG. 1) to a physiological profile 22 (FIG. 1) of patient P to thereby ascertain whether or not a physiological status of patient P is critical.

A critical physiological status of patent P is a physiological status of patient P defined by the intervention system as a physiological status of patient P that necessitates a generation of an updated anatomical roadmap 82 for purposes of facilitating a navigation of interventional robot 30 within the patient anatomy.

An example of a critical physiological status of a patient includes, but is not limited to, basic physiological parameters (e.g., respiration, heart rate, etc.) of the patient indicating an unacceptable risk of anxiety, panic, claustrophobic episodes, etc. in a patient during an interventional procedure.

If robot control 90 ascertains physiological status of patient P is non-critical, then robot control 90 loops back to stage S104 and stage S106 until such time robot control 90 ascertains robot control 90 is proximate to a critical anatomical location within anatomical roadmap 82a or robot control 90 ascertains physiological status of patient P is critical.

If robot control 90 ascertains robot control 90 is proximate to a critical anatomical location within anatomical roadmap 82a or if robot control 90 ascertains physiological status of patient P is critical, then robot control 90 proceeds to a stage S108 of flowchart 100 to (1) pause the robot navigation and to inform modality control 80 to (1) generate X-ray actuation commands 85 for controlling X-ray modality 10 to acquire a new X-ray image 61b of a heart of patient P in accordance with intervention plan 81a to thereby generate an updated anatomical roadmap 82b, preferably a high resolution X-ray image 61b taken at the same or different orientation relative to the patient than X-ray image 61a and to (2) register X-ray image 61b, anatomical roadmap 82b and interventional robot 30 as known in the art of the present disclosure.

In one embodiment, roadmap 82b is generated from a X-ray image 61b by applying image processing techniques of known in the art of the present disclosure including an edge detection to reveal boundaries of anatomical structures, a thresholding to remove noise and minor variances in pixel values, and a segmentation and classification to identify connected anatomical structures. Once the anatomical structure is revealed, the anatomical structure may be referenced semantically to a clinical model to determine a path within X-ray image 6b for robot 30 to traverse. The path is determined in the coordinate system of the X-ray image 61b, and the image is registered to robot 30 via registration techniques as known in the art of the present disclosure, thus informing the robot's trajectory.

A fine robot navigation of stage S108 further involves robot control 90 (4) navigating updated anatomical roadmap 82b a in accordance with intervention plan 81a to thereby generate robot actuation commands 92 whereby interventional robot 30 correspondingly resumes a navigation through the anatomical region of patient P.

This navigation is considered a fine robot navigation because the field-of-view of the anatomical roadmap 82a is intended to be of a smaller area of pathways through one or more anatomical structures AS to facilitate a slower, more precise navigation of anatomical roadmap 82b.

In practice, the control of X-ray modality 10 by modality control 80 may be in one or more modes beneficial to the generation of the updated anatomical roadmap 82b.

In one mode, modality control 80 may control an activation and a deactivation of X-ray imaging modality 10 to minimize radiation exposure by the patient P.

In a second mode, modality control 80 may control one or more operational parameters of X-ray imaging modality 10, such as, for example, a modulation of X-ray framerate and radiation energy.

In a third mode, modality control 80 may control synchronize an activation of X-ray imaging modality 10 with a physiological cycle of the patient, such as, for example, a heartbeat of patient P.

In a third mode, modality control 80 may control an orientation of X-ray imaging modality relative to patient P to acquire an optical viewpoint of the anatomical roadmap.

In a fourth mode, modality control 80 may control an injection of a contrast agent into patient P, particularly based on a position of interventional robot 30 within the anatomical region of patient P.

In support of the image acquisition of stage S108, robot control 90 may command a movement of interventional robot 30 from within the field-of-view of X-ray imaging modality 10 to thereby reduce any artefacts induced by interventional robot 30 into X-ray image 61b. More particularly, in view of robot control 90 knowing robot poses 91 executed prior to robot control 90 being proximate the critical anatomical location or the physiological status of patient P being deemed critical, then robot control reproduce such robot poses 91 subsequent to the acquisition of X-ray image 61b.

Further, if modality control 80 fails to acquire new X-ray image 61b during stage S108, robot control 90 may execute an inverse of previous robot poses 91 to a point whereby robot control 90 is not proximate to a critical anatomical location and a physiological status of patient P is non-critical.

Flowchart 100 is terminated upon a final positioning of interventional robot 30 within the anatomical region of patient P in accordance with the intervention plan 81a.

Figure 3:
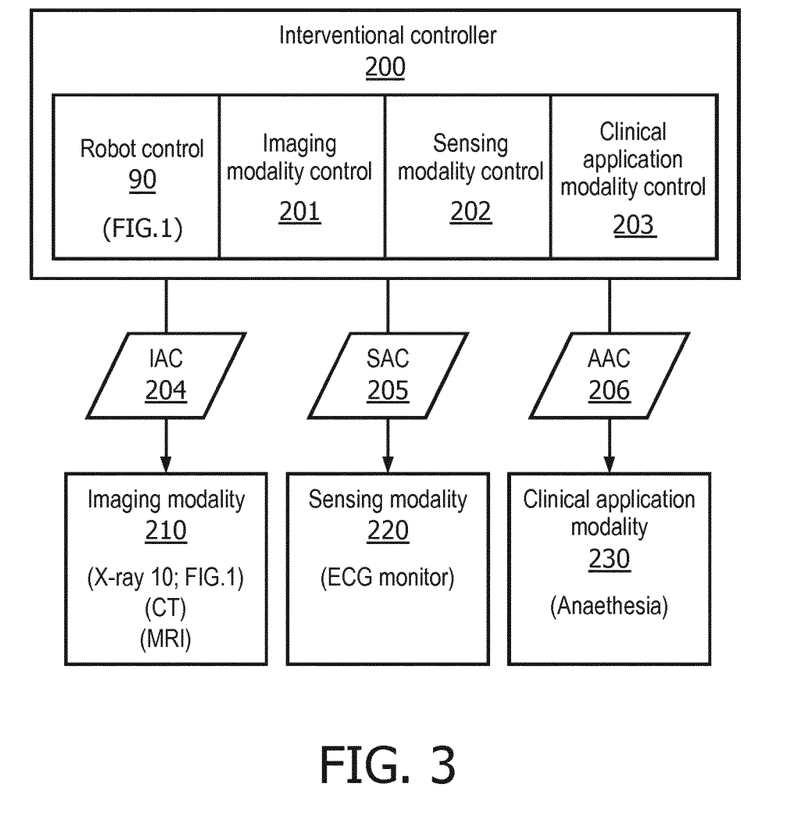
FIG. 3 illustrates a second exemplary embodiment of an interventional controller in accordance with the inventive principles of the present disclosure.

To facilitate a further understanding of the various inventions of the present disclosure, the following description of FIG. 3 teaches basic inventive principles associated with an interventional controller of the present disclosure further controlling a sensing modality and a clinical application modality. From this description, those having ordinary skill in the art will appreciate how to apply the inventive principles of the present disclosure for making and using additional embodiments of interventional controllers of the present disclosure.

An interventional controller 200 employs robot control 90 as previously described in the present disclosure. If robot control 90 ascertains robot control 90 is proximate to a critical anatomical location within anatomical roadmap 82a (e.g., stage 104 of FIG. 2) or if robot control 90 ascertains physiological status of patient P is critical (e.g., stage S106 of FIG. 2), then robot control will inform an imaging modality control 201, a sensing modality control 202 and a clinical application modality control 203.

In response to being informed by robot control 90 of the criticality of the procedure, imaging modality control 201 generates image actuation commands 204 for controlling an imaging modality 204 to acquire a new image of the anatomical region of the patient and to generate an updated roadmap as previously described in the present disclosure.

In response to being informed by robot control 90 of the criticality of the procedure, sensing modality control 201 generates sensing actuation commands 204 to control an activation and a deactivation of a sensing modality 220 and/or to control one or more operational parameters of sensing modality 220. Examples of sensing modality 220 include an ECG monitor wherein the display of the ECG, SpO2, NIBP, and CO2 are modified to provide better clarity as to disposition of patient P.

In response to being informed by robot control 90 of the criticality of the procedure, clinical application modality control 202 generates application actuation commands 206 to control an activation and a deactivation of a clinical application modality 230 and/or to control one or more operational parameters clinical application modality 230. Examples of clinical application modality 230 include an anaesthesia modality wherein blood pressure, heart rate control, ventilator, etc. are controlled depending upon of the criticality of the procedure.

Referring to FIGS. 1-3, those having ordinary skill in the art of the present disclosure will appreciate numerous benefits of the inventions of the present disclosure including, but not limited to, a minimal degree of imaging of an anatomical region of a patient during an interventional procedure that is beneficial to the patient, such as, for example, a minimal degree of X-ray imaging of an anatomical region of a patient during an interventional procedure that results in a significant reduction in radiation exposure to a patient.

Further, as one having ordinary skill in the art will appreciate in view of the teachings provided herein, structures, elements, components, etc. described in the present disclosure/specification and/or depicted in the Figures may be implemented in various combinations of hardware and software, and provide functions which may be combined in a single element or multiple elements. For example, the functions of the various structures, elements, components, etc. shown/illustrated/depicted in the Figures can be provided through the use of dedicated hardware as well as hardware capable of executing software in association with appropriate software for added functionality. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Having described preferred and exemplary embodiments of novel and inventive image guidance of steerable introducers, and systems and methods incorporating such image guidance of steerable introducers, (which embodiments are intended to be illustrative and not limiting), it is noted that modifications and variations can be made by persons skilled in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device/system or such as may be used/implemented in/with a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. An interventional controller for controlling execution of an interventional procedure by an interventional robot, the interventional controller comprising:
   at least one processor configured to:
      control a navigation of the interventional robot within an anatomical region of a patient in accordance with an anatomical roadmap of the anatomical region and an interventional plan,
      detect an occurrence of the navigation of the interventional robot being proximate to a critical anatomical location within the anatomical roadmap, and
      in response to the detected occurrence:
         pause the navigation of the interventional robot within the anatomical region of the patient,
         autonomously control an interventional imaging of the anatomical region of the patient by an interventional imaging modality, generate an updated anatomical roadmap of the anatomical region from the interventional imaging of the anatomical region of the patient, and control a resumed navigation of the interventional robot within the anatomical region of the patient in accordance with the updated anatomical roadmap and the interventional plan.

2. The interventional controller of claim 1, wherein the critical anatomical location is one of:

a location within the anatomical roadmap corresponding to an anatomical branch;

a location within the anatomical roadmap corresponding to an exit point of the anatomical roadmap;

a location within the anatomical roadmap corresponding to a surface of an anatomical structure;

a location within the anatomical roadmap corresponding to a range of motion of an anatomical structure;

a location within the anatomical region corresponding to an interventional task in accordance with the intervention plan; or and a location within the anatomical region corresponding to an application of force by the interventional robot upon an anatomical structure within the anatomical region.

3. The interventional controller of claim 1, wherein the at least one processor is configured to autonomously control the interventional imaging of the anatomical region of the patient by the interventional imaging modality by the at least one processor further configured to at least one of:

control an activation and a deactivation of the interventional imaging modality;

control at least one operational parameter of the interventional imaging modality;

control the imaging of the anatomical region by the interventional imaging modality in synchronization with a physiological cycle of the patient;

control an orientation of the interventional imaging modality relative to the patient based on a position of the interventional robot within the anatomical region; and control an injection of an imaging agent into the patient based on a position of the interventional robot within the anatomical region.

4. The interventional controller of claim 1, wherein the at least one processor is further configured to:

detect a critical physiological status of the patient during the navigation of the interventional robot within the anatomical region of the patient, and in response to the detected critical physiological status, the at least one processor is further configured to:

pause the navigation of the interventional robot within anatomical region of the patient, autonomously control the interventional imaging of the anatomical region of the patient by the interventional imaging modality, generate the updated anatomical roadmap of the anatomical region from the interventional imaging of the anatomical region of the patient, and control the resumed navigation of the interventional robot within the anatomical region of the patient in accordance with updated anatomical roadmap of the anatomical region and the interventional plan.

5. The interventional controller of claim 4, wherein the at least one processor is further configured to:

receive patient sensing data informative of an intervention physiological status of the patient;

analyze the intervention physiological status of the patient in view of a physiological profile of the patient; and designate the intervention physiological status of the patient as one of a non-critical physiological status or the critical physiological status of the patient based on an analysis of the intervention physiological status of the patient in view of a physiological profile of the patient.

6. The interventional controller of claim 1, wherein the interventional imaging modality is an X-ray modality.

7. The interventional controller of claim 1, wherein the at least one processor is further configured to at least one of:

in response to the detected occurrence, autonomously control an operation of a first sensing modality; and in response to detection of a critical physiological status of the patient during the navigation of the interventional robot within the anatomical region of the patient, autonomously control an operation of a second sensing modality.

8. The interventional controller of claim 1, wherein the at least one processor is further configured to at least one of:

in response to the detected occurrence, autonomously control an operation of a first clinical application modality; and in response to detection of a critical physiological status of the patient during the navigation of the interventional robot within the anatomical region of the patient, autonomously control an operation of a second clinical application modality.

9. The interventional controller of claim 1, wherein the at least one processor is configured to execute modules stored in memory including:

a modality control module and a robot control module configured to control an execution of the interventional procedure by the interventional robot and the interventional imaging modality, wherein the robot control module is configured to control the navigation of the interventional robot within the anatomical region of the patient in accordance with the anatomical roadmap of the anatomical region, wherein the robot control module is further configured to detect the occurrence of the navigation of the interventional robot within the anatomical region being proximate to the critical anatomical location within the anatomical roadmap, and wherein, in response to the detected occurrence:

the robot control module is further configured to pause the navigation of the interventional robot within anatomical region of the patient, the modality control module is configured to autonomously control the interventional imaging of the anatomical region of the patient by the interventional imaging modality, the modality control module is further configured to generate the updated anatomical roadmap of the anatomical region from the interventional imaging of the anatomical region of the patient, and the robot control module is further configured to control the resumed navigation of the interventional robot within the anatomical region of the patient in accordance with the updated anatomical roadmap of the anatomical region and the interventional plan.

10. The interventional controller of claim 9, wherein the critical anatomical location is one of:

a location within the anatomical roadmap corresponding to an anatomical branch;

a location within the anatomical roadmap corresponding to an exit point of the anatomical roadmap;
a location within the anatomical roadmap corresponding to a surface of an anatomical structure;
a location within the anatomical roadmap corresponding to a range of motion of an anatomical structure;
a location within the anatomical region corresponding to an interventional task in accordance with the intervention plan;
a location within the anatomical region corresponding to an application of force by the interventional robot upon an anatomical structure within the anatomical region.

11. The interventional controller of claim 9, wherein the modality control module is configured to autonomously control the interventional imaging of the anatomical region of the patient by the modality control module further configured to at least one of:
control an activation and a deactivation of the interventional imaging modality;
control at least one operational parameter of the interventional imaging modality;
control the interventional imaging of the anatomical region in synchronization with a physiological cycle of the patient;
control an orientation of the interventional imaging modality relative to the patient based on a position of the interventional robot within the anatomical region; and
control an injection of an imaging agent into the patient based on a position of the interventional robot within the anatomical region.

12. The interventional controller of claim 9,
wherein the modality control module is further configured to detect a critical physiological status of the patient during the navigation of the interventional robot within the anatomical region of the patient; and
wherein in response to the detected critical physiological status:
the robot control module is further configured to pause the navigation of the interventional robot within anatomical region of the patient,
the modality control module is further configured to autonomously control the interventional imaging of the anatomical region of the patient by the interventional imaging modality,
the modality control module is further configured generate the updated anatomical roadmap of the anatomical region from the interventional imaging of the anatomical region of the patient, and
the robot control module is further configured to control the resumed navigation of the interventional robot within the anatomical region of the patient in accordance with the updated anatomical roadmap of the anatomical region and the interventional plan.

13. The interventional controller of claim 12, wherein the modality control module is further configured to:
receive patient sensing data informative of an intervention physiological status of the patient;
analyze the intervention physiological status of the patient in view of a physiological profile of the patient; and
designate the intervention physiological status of the patient as one of a non-critical physiological status or the critical physiological status of the patient based on an analysis of the intervention physiological status of the patient in view of a physiological profile of the patient.

14. The interventional controller of claim 12, wherein the at least one processor is further configured to at least one of:
in response to the detected occurrence, autonomously control an operation of a first sensing modality; and
in response to the detected critical physiological status, autonomously control an operation of a second sensing modality.

15. The interventional controller of claim 12, wherein the at least one processor is further configured to at least one of:
in response to the detected occurrence, autonomously control an operation of a first clinical application modality; and
in response to the detected critical physiological status, autonomously control an operation of a second clinical application modality.

16. An intervention method for navigating an interventional robot, the intervention method comprising:
controlling a navigation of the interventional robot within an anatomical region of a patient in accordance with an anatomical roadmap of the anatomical region and an interventional plan;
detecting an occurrence of the navigation of the interventional robot reaching a critical anatomical location within the anatomical roadmap; and
in response to the detected occurrence:
pausing the navigation of the interventional robot within the anatomical region of the patient,
autonomously controlling an interventional imaging of the anatomical region of the patient by an interventional imaging modality,
generating an updated anatomical roadmap of the anatomical region from the interventional imaging of the anatomical region of the patient, and
controlling a resumed navigation of the interventional robot within the anatomical region in accordance with the updated anatomical roadmap of the anatomical region and the interventional plan.

17. The intervention method of claim 16, wherein the critical anatomical location is one of:
a location within the anatomical roadmap corresponding to an anatomical branch;
a location within the anatomical roadmap corresponding to an exit point of the anatomical roadmap;
a location within the anatomical roadmap corresponding to a surface of an anatomical structure;
a location within the anatomical roadmap corresponding to a range of motion of an anatomical structure;
a location within the anatomical region corresponding to an interventional task in accordance with the intervention plan; or
a location within the anatomical region corresponding to an application of force by the interventional robot upon an anatomical structure within the anatomical region.

18. The intervention method of claim 16, wherein autonomously controlling the interventional imaging of the anatomical region of the patient by the interventional imaging modality includes at least one of:
controlling an activation and a deactivation of the interventional imaging modality;
controlling at least one operational parameter of the interventional imaging modality;
controlling the interventional imaging of the anatomical region by the interventional imaging modality in synchronization with a physiological cycle of the patient;

controlling an orientation of the interventional imaging modality relative to the patient based on a position of the interventional robot within the anatomical region; and controller controlling an injection of an imaging agent into the patient based on a position of the interventional robot within the anatomical region.

19. The intervention method of claim 16, further comprising detecting a critical physiological status of the patient during the initial navigation of the interventional robot within the anatomical region of the patient; and in response to the detected critical physiological status:
pausing the navigation of the interventional robot within anatomical region of the patient,
autonomously controlling an interventional imaging of the anatomical region of the patient by an interventional imaging modality,
generating an updated anatomical roadmap of the anatomical region from the interventional imaging of the anatomical region of the patient, and
controlling the resumed navigation of the interventional robot within the anatomical region of the patient in accordance with the updated anatomical roadmap of the anatomical region and the interventional plan.

20. The intervention method of claim 19, further comprising:

receiving patient sensing data informative of an intervention physiological status of the patient;

analyzing the intervention physiological status of the patient in view of a physiological profile of the patient; and designating the intervention physiological status of the patient as one of a non-critical physiological status or the critical physiological status of the patient based on an analysis of the intervention physiological status of the patient in view of the physiological profile of the patient.

* * * * *